United States Patent

Walpole et al.

[11] Patent Number: 6,107,293
[45] Date of Patent: Aug. 22, 2000

[54] TACHYKININ ANTAGONISTS

[75] Inventors: Christopher Simon John Walpole, Quebec, Canada; Mahavir Prashad, Montville; Denis Har, Harrison, both of N.J.

[73] Assignee: Novaris AG, Basel, Switzerland

[21] Appl. No.: 09/341,626

[22] PCT Filed: Dec. 29, 1997

[86] PCT No.: PCT/EP97/07307

§ 371 Date: Jul. 14, 1999

§ 102(e) Date: Jul. 14, 1999

[87] PCT Pub. No.: WO98/31704

PCT Pub. Date: Jul. 23, 1998

[30] Foreign Application Priority Data

Jan. 14, 1997 [GB] United Kingdom ............... 9700597

[51] Int. Cl.[7] .................. A61K 31/517; A61K 31/536; A61K 31/5415; C07D 403/04; C07D 413/04
[52] U.S. Cl. .................. 514/227.2; 514/230.5; 514/260; 514/367; 514/375; 514/395; 544/50; 544/90; 544/92; 544/287; 544/292; 548/162; 548/222; 548/306.1; 548/538
[58] Field of Search .................. 544/292, 287, 544/90, 92, 50; 548/162, 222, 306.1, 538; 514/227.2, 230.5, 260, 367, 375, 395

[56] References Cited

FOREIGN PATENT DOCUMENTS 0147211   7/1985   European Pat. Off. .
0443132 A1   8/1991   European Pat. Off. .

OTHER PUBLICATIONS

Krantz et al., J. Med. Chem. 1990, 33, pp. 464–479.

*Primary Examiner*—Mukund J. Shah
*Attorney, Agent, or Firm*—Carol A. Loeschorn

[57] ABSTRACT

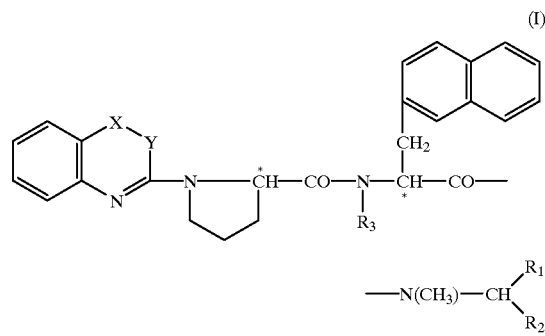

Compounds of formula (I) wherein X is —CH$_2$—, —CO— or direct linkage, Y is —O—, —S— or —NH—, R$_1$ is phenyl, R$_2$=H or phenyl and R$_3$ is H or —CH$^3$— and their pharmaceutically acceptable salts have tachykinin antagonist activity and are useful as pharmaceuticals e.g. for the treatment of pain and migraine.

9 Claims, No Drawings

TACHYKININ ANTAGONISTS

The present invention relates to novel compounds having tachykinin antagonist activity, processes for their production, pharmaceutical compositions comprising them and their use as pharmaceuticals.

More particularly the present invention provides a compound of formula I

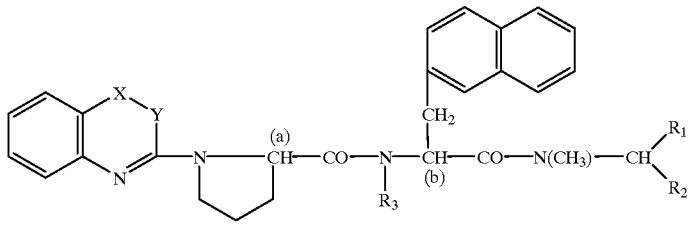

(I)

wherein
X is —CH$_2$—, —CO— or a direct linkage,
Y is —O—, —S— or —NH—,
R$_1$ is phenyl,
R$_2$ is hydrogen or phenyl, and
R$_3$ is hydrogen or methyl,
or acid addition salt thereof.

In formula I, the following significances are preferred, individually or in any combination or sub-combination:
a) X is —CO— or a direct linkage, especially —CO—;
b) Y is —O— or —NH—, especially —NH—;
c) X is —CO— and Y is —NH—.
d) R$_2$ is hydrogen;
e) R$_3$ is methyl;

Compounds of formula I in which X is —CH$_2$— or —CO— and Y is —NH— exist in tautomeric form, e.g. comprising the structures

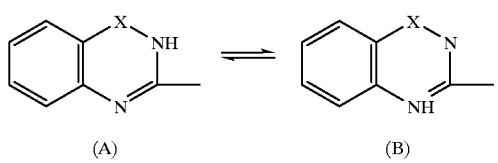

(A)   (B)

The present invention is to be understood as including such tautomeric forms and formula I, as well as the formulae for corresponding intermediates as hereinafter described, are accordingly to be understood as embracing both the structures A and B.

Compounds of formula I exist in free form and in acid addition salt form. The present invention is to be understood as including both free compounds of formula I and their acid addition salts. Suitable pharmaceutically acceptable acid addition salts for use in accordance with the present invention include e.g. hydrochloride salts.

Compounds of the invention comprise two asymmetric carbon atoms [marked (a) and (b) in formula I]. The compounds accordingly exhibit optical isomerism. Individual isomers may be obtained in conventional manner, e.g. by synthesis using optically active starting materials or by separation of initially obtained isomeric mixtures, for example employing chromatographic techniques using a chiral support or by recrystallisation of diastereomeric salt forms. The present invention is to be understood as embracing both individual isomers of compounds of formula I in pure or substantially pure form as well as mixtures, e.g. racemic and diastereomeric mixtures thereof unless otherwise specified.

In formula I each of the carbon atoms (a) and (b) suitably has the (S)-configuration. More suitably both carbon atoms (a) and (b) have the (S)-configuration. Accordingly, in a preferred aspect the present invention provides a compound of formula I as hereinbefore defined wherein the carbon atoms (a) and (b) both have the (S)-configuration in pure or substantially pure form, e.g. comprising less than 10%, more preferably less than 5%, e.g. less than 2% of other isomeric forms.

The present invention further provides a process for the production of a compound of formula I as hereinbefore defined or acid addition salt thereof, which process comprises a) reacting a compound of formula II

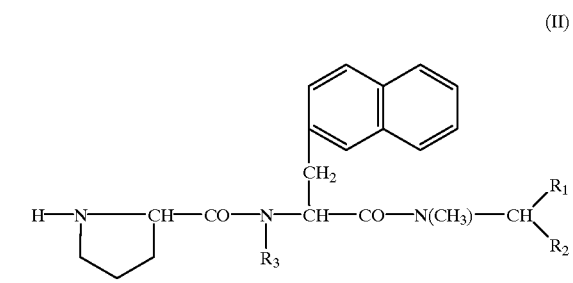

(II)

wherein R$_1$, R$_2$ and R$_3$ have the meanings given for formula I with a compound of formula III

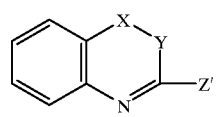

(III)

wherein X and Y have the meanings given for formula I and Z' is a leaving group;

b) for the production of a compound of formula I wherein X is —CO— and Y is —O— or —S—, reacting a compound of the formula II as defined above with a compound of formula IV

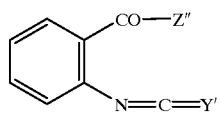

(IV)

wherein Z" is a leaving group and Y' is —O— or —S—; or c) for the production of a compound of formula I wherein X is —CO— and Y is —NH—, treating a compound of formula V

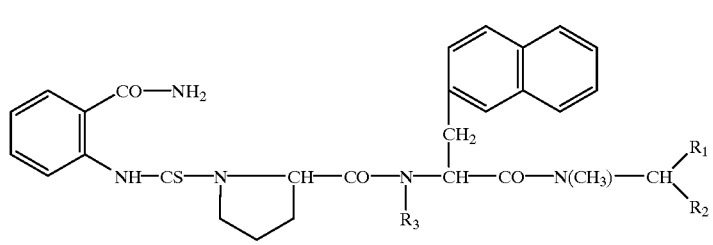

wherein $R_1$, $R_2$ and $R_3$ have the meanings given for formula I with an alkyl halide;
and recovering the compound of formula I thus obtained in free or acid addition salt form.

Suitable leaving groups as Z' for process step a) are halogen or, when X is —CH$_2$— also —NCN. Process step (a) may be carried out in accordance with standard procedures, e.g., when Z' is halogen in the presence of an acid binding agent, e.g. organic base such as triethylamine, in an inert organic solvent at elevated temperature. Suitably, when Z' is halogen this is chlorine. Suitable solvent media include, for example, isopropyl acetate (e.g. when X is —CO—) dioxane (e.g. when X is a direct bond and Y=—O— or —S—), xylene (e.g. when X is a direct bond and Y=—NH—), or isopropanol (e.g. when X is —CH$_2$—), with reaction at temperatures of e.g. from 50° to 80° C. up to reflux.

In one variant according to process step (a), X is —CO— and Y is —NH—. In accordance with this variant Z' may be halogen, e.g. chlorine. Also $R_2$ may be hydrogen and $R_3$ may be methyl. A procedure for carrying out process step (a) in accordance with this variant is described in Example 7 hereinafter.

For process step (b), suitable leaving groups as Z" include halogen, e.g. chlorine. Reaction may be performed in accordance with conventional procedures, for example, in an inert solvent or diluent such as ethyl acetate, optionally in the presence of an acid binding agent, e.g. organic base such as triethylamine, e.g. at a temperature of from 20 to 70° C.

Process step (c) may also be carried out in accordance with conventional procedures, for example, in the presence of methyl iodide in an inert solvent or diluent such as ethyl acetate, e.g. at a temperature of from 10 to 30° C.

Compounds of the formula II may be prepared in accordance with the methods disclosed in International Patent Application No. PCT/EP95/04910 (=Publication no. WO 96/18643 published Jun. 20, 1996—see, in particular, pages 7 to 9) or as described in Example 7, parts i) and ii) below.

Starting materials of formula III and IV are commercially available, otherwise known from the art or may be prepared analogously to the known compounds. [See e.g. Vigne et al., J. Heterocyclic Chem., 13(4), 921–924 (1976) and Garrett et al. Tetrahedron 45(3), 829–834 (1989)]

Compounds of formula III wherein X=—CO— and Y=—NH— may also be prepared for example:

(d) by treating 2,4-dichloroquinazoline, i.e. the compound of formula VI

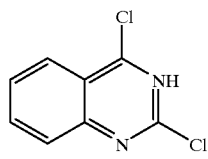

with a base for, example alkali metal hydroxide, for example NaOH. Reaction is suitably performed in an aqueous medium, e.g. at temperatures of from 15–25 or 30° C., e.g. as described in Example 7 hereinafter.

Compound VI may in turn be produced, for example:

(e) by reaction of 2,4-dioxo-1,4-dihydro-quinazoline (or benzoyiene urea), i.e. the compound of formula VII

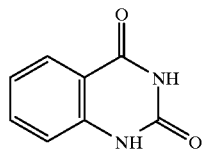

with phosphorous oxychloride (POCl$_3$). This process is suitably performed in the presence of an organic base, for example, trialkylamine, e.g. tripropylamine, e.g. at temperatures of from ca. 15° C. to reflux, e.g. as also exemplified in Example 7.

Process steps (d) and (e) above are also novel independently or in relation to the synthesis of the corresponding compound of formula I and thus also constitute part of the present invention.

Starting materials of formula V may be prepared from compounds of formula II, e.g. in accordance with the following reaction scheme:

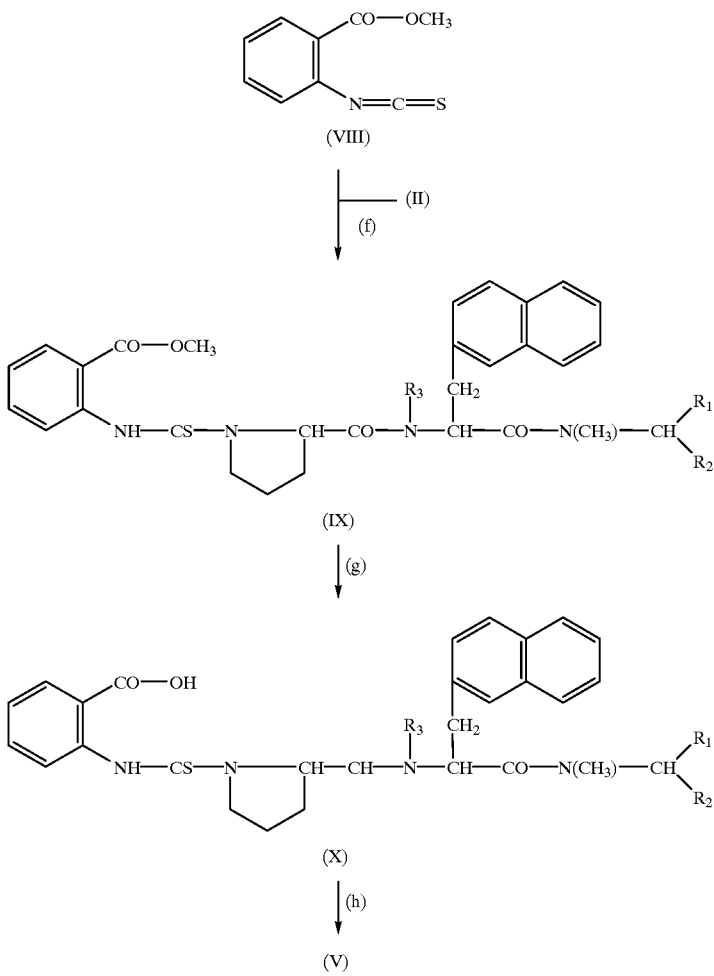

Suitable reaction conditions for the above steps (f) through (h) are as hereinafter described in relation to Example 2 below.

The following examples are illustrative of the processes for the production of the compounds of the invention.

EXAMPLE 1

Process Step (b)

Preparation of 1-(4-oxo-4H-benzo[d][1,3]-oxazin-2-yl)-(S)-prolyl-(S)-3-(2-naphthyl)alanyl-N-benzyl-N-methylamide (Formula I: X=—CO—: Y=—O—: $R_1$=phenyl: $R_2$ and $R_3$=H: C atoms (a) and (b)-(S)-configuration.)

(S)-prolyl-(S)-3-(2-naphthyl)alanyl-N-benzyl-N-methylamide (formula II) (6.53 g) is dissolved in dry toluene (30 ml) and the solution is stirred at 80° C. 2-isocyanatobenzoylchloride (Vigne et al., loc. cit.: 1.42 g) is added dropwise in 200 ml dry toluene and stirring continued for 20 mins. Solvent is removed under vacuum and the product purified by flash column chromatography (silica, ethyl acetate/cyclohexane 2:1) to yield the title compound as a colourless glass: m.p. 78–85° C.: TLC, cyclohexane/ethyl acetate 1:4, Rf=0.56.

The formula II starting material for the above process is produced in accordance with or analogously to the methods described in the aforementioned International Patent Publication no. WO 96/18643, examples IA to ID.

EXAMPLE 2

Process Step (c)

Preparation of 1-(4-oxo-1,4-dihydro-quinazolin-2-yl)-(S)-prolyl-(S)-3-(2-naphthyl)alanyl-N-benzyl-N-methylamide (Formula I: X=—CO—: Y=—NH—: $R_1$=phenyl, $R_2$ and $R_3$=H: atoms (a) and (c)-(S)-configuration).

2-carbamoylphenylthiocarbamoyl)-(S)-prolyl-(S)-3-(2-naphthyl)alanyl-N-benzyl-N-methylamide (Formula IV) (0.54 g) is dissolved in ethyl acetate 20 ml and methyliodide (0.145 g) is added with stirring. The reaction mixture is stirred overnight and the solvent evaporated under vacuum. The obtained solid is purified by flash column chromatography (silica, $CH_2Cl_2/CH_3OH$ 25:1) to yield the title compound as a colourless amorphous solid: m.p.=110–115° C.: TLC $CH_2Cl_2/CH_3OH$ 20:1, Rf=0.35: $[\alpha]_D$=−122.3° (c=1, $CHCl_3$). Hydrochloride salt—m.p.=150° with foaming.

The formula IV starting material for the above process is produced as follows:

Process Step (f)

Preparation of 2-methoxcarbonylthiocarbamoyl-(S)-prolyl-(S)-3-(2-naphthyl)alanyl-N-benzyl-N-methylamide (Formula IX)

2-methoxycarbonylphenylisothiocyanate (0.196 g) and (S)-prolyl-(S)-3-(2-naphthyl)alanyl-N-benzyl-N-methylamide (0.46 g) are dissolved in dioxane (50 ml) and stirred at room temperature overnight. The resulting solution is evaporated and purified by flash column chromatography (silica, cyclohexane/ethyl actate 1:1), to yield the title compound.

Process Step (g)
Preparation of 2-carboxyphenylthiocarbamoyl-(S)-prolyl-(S)-3-(2-naphthyl)alanyl-N-benzyl-N-methylamide (formula X)

The product of step (f) (0.65 g) is dissolved in methanol (10 ml) and 5N NaOH (1 ml) is added. The reaction mixture is stirred at room temperature for 4 hours, 0.1N HCl (100 ml) is added and the whole extracted with ethyl acetate. The solvent is removed under vaccum to yield the title compound as a colourless glass: TLC cyclohexane/ethyl acetate 1:1, Rf=0.02.

Process Step (h)
Preraration of 2-carbamoylphenylthiocarbamoyl)-(S)-prolyl-(S)-3-(2-naphthyl)alanyl-N-benzyl-N-methylamide (Formula XI)

The product of step (g) (0.62 g) is dissolved in dry tetrahydrofuran (20 ml), N-methylmorpholine is added (111 mg) and the reaction mixture cooled on a salt-ice bath. Isobutylchloroformate (0.15 g) is slowly added and the reaction mixture stirred at −10° C. for 10 mins. Ammonium hydroxide solution (2 ml, saturated) is added and the reaction mixture stirred overnight before removal of the solvent under vacuum. The obtained title compound is purified by flash column chromatography (silica, $CH_2Cl_2/CH_2OH$ 25:1) to be recovered as a colourless glass.

EXAMPLE 3

Process Step (a)
Preparation of 1-(benzoxazol-2-yl)-(S)-prolyl-(S)-3-(2-naphthyl)alanyl-N-benzyl-N-methylamide. (Formula I: X=direct linkage, Y=—O—, $R_1$=phenyl, $R_2$ and $R_3$=H: C atoms (a) and (b)-(S)-configuration).

(S)-Prolyl-(S)-3-(2-naphthyl)alanyl-N-benzyl-N-methylamide (0.96 g) is dissolved in dioxane (10 ml) and triethylamine (0.34 ml). 2-chlorobenzoxazole (0.34 g) is added and the reaction mixture heated under reflux for 14 hours. The solvent is removed under vacuum, the product is dissolved in ethyl acetate washed with $H_2O$ and saturated brine and the solvent removed under vacuum. The product is purified by flash column chromatography (silica, ethyl acetatelcyclohexane 2:1) to yield the title compound as a colourless glass: m.p.=63–68° C.: TLC cyclohexane/ethyl acetate 1:1, Rf=0.15.

EXAMPLE 4

Process Step (a)
Preparation of 1-(1H-benzimidazol-2-yl)-(S)-prolyl-(S)-3-(2-naphthyl)alanyl-N-benzyl-N-methylamide (Formula I: X=direct linkage: Y=—NH—: $R_1$=phenyl: $R_2$ and $R_3$=H: C atoms (a) and (b)-(S)-configuration.)

The title compound is prepared analogously to Example 3 starting from 2-chlorobenzimidazole with reaction under re-flux in xylene: m.p.=110–114° C.: TLC cyclohexane/ethyl acetate 1:4, Rf=0.08.

EXAMPLE 5

Process Step (a)
Preparation of 1-(4H-benzo[d][1,3]oxazin-2-yl)-(S)-prolyl-(S)-3-(2-naphthyl)alanyl-N-benzyl-N-methylamide (Formula I: X=—$CH_2$—: Y=—O—, $R_1$=phenyl: $R_2$ and $R_3$=H: C atoms (a) and (b)-(S)-configuration.)

(S)-Prolyl-(S)-3-(2-naphthyl)alanyl-N-benzyl-N-methylamide (0.75 g) and 2-cyanoimino-4H-benzo[d][1,3] oxazine (Garrett et al., loc. cit. 0.75 g) (0.5 g) are combined in 6 ml isopropanol/$H_2O$ (1:5) and the mixture heated to reflux for 4 hrs. The reaction product is poured into $H_2O$ (150 ml) and the product extracted with ethyl acetate, the solvent evaporated and the residue purified by flash column chromatography (silica, cyclohexane/ethylacetate 1:3) to yield the title compound as a colourless glass: m.p.=60–65° C.; TLC cyclohexane/ethylacetate 1:4, Rf=0.40.

EXAMPLE 6

Process Step (c)
Preparation of 1-(4-oxo-1,4-dihydroquinazolin-2-yl)-(S)-prolyl-(S)-[N-methyl-3-(2-naphthyl)alanyl]-N-benzyl-N-methylamide (Formula I: X=—CO—: Y=—NH—: $R_1$=phenyl: $R_2$=H: $R_3$=—$CH_3$: atoms (a) and (c) both-(S)-configuration.)

The title compound is prepared analogously to Example 2 starting from (S)-prolyl-(S)-[N-methyl-3-(2-naphthyl) alanyl]-N-benzyl-N-methylamide: m.p.=112–113° C.: TLC Silica, ethyl acetate Rf=0.22.

The starting material for the above process is produced analogously to or in accordance with the methods described in the aforementioned International Patent Publication no. WO 96/18634 in relation to Examples 27 and 29, or as in Example 7 following.

EXAMPLE 7

Process Step (a)
Large scale preparation of 1-(4-oxo-1,4-dihydroquinazolin-2-yl)-(S)-prolyl-(S)-3-[N-methyl-(2-napthyl)alanyl]-N-benzyl-N-methylamide (cf. Example 6) is suitably performed as follows:

STEP a
A 5-L, 4-necked, round-bottomed flask, equipped with a mechanical stirrer, digital thermometer, a 60 ml addition funnel, nitrogen inlet-outlet, and heating mantle is charged with (S)-prolyl-(S)-3-[N-methyl-(2-naphthyl)alanyl]-N-benzyl-N-methyl amide (95.1 g), 40.0 g 2-chloro-4(3H)-quinazolone [formula III: X=—CO—, Y=—NH—, $R^1$=Cl] 2 and 1.6 liters isopropyl acetate. The suspension is heated to 71° C. (internal temperature; external temperature 83° C.) and 45.7 g triethylamine are added over a period of 5 minutes. The mixture is refluxed (internal temperature 88.7° C.; external temperature 112° C.) for 3 h. The reaction mixture is cooled to 21° C. 1.5 liters distilled water are added and the layers separated. The aqueous layer is extracted with 1×750 ml ethyl acetate. The organic layers are combined, washed with 1×750 ml brine and concentrated at a bath temperature 50° C. The obtained crude product is dissolved in 300 ml ethyl acetate and loaded onto a chromatography column.

Chromatographic Conditions:
1000 g silica gel, EM Science 60–230 mesh; Column dimensions: 25 cm (I)×10.5 cm (id). Eluant: 100% ethylacetate, followed by 5% ethanol/ethyl acetate.

A total of 22 fractions are collected at 350–500 ml/fraction. Fractions 5 to 21 are combined and concentrated at a bath temperature of 50° C. under vacuum (100 m bar).

The residue is dissolved in 3×400 ml absolute ethanol and concentrated at a bath temperature of 50° C. under vacuum (100 mbar). The obtained solid is dried at 50° C. under vacuum (100 mbar) for 18 hrs. to give the title compound: m.p.=175–176° C.

(S)-Prolyl-(S)-3-[N-methyl-(2-naphthyl)alanyl]-N-benzyl-N-methylamide required as starting material for the above process is prepared as follows:

i) A 4-necked, 5-liter, round bottomed flask, equipped with a mechanical stirrer, a nitrogen inlet-outlet and a heating mantle is charged with 238.0 g Boc-(S)-3-(2-naphthyl)-alanyl-N-benzyl-N-methylamide [prepared in accordance with the methods described in Example 34 step III of the aforementioned International Patent Publication no. WO 96/18634] and 2 liters N,N-dimethylformamide to obtain a solution. 433 g $Ag_2O$ and 230 ml iodomethane are added. The mixture is heated to an internal temperature of 60° C. (external temperature 70° C.) and the resulting black slurry stirred at this temperature for 17 hours. The progress of the reacton is monitored by HPLC. The obtained mixture is concentrated to collect any unreacted iodomethane under vacuum with appropriate cold traps installed (~−78° C., 20 mm Hg). The mixture is filtered through a Buchner funnel and the solids washed with 1×1 liter dichloromethane. The filtrate is washed with 1×9 liters distilled $H_2O$. The aqueous layer is back-extracted with 2×1.8 liters dichloromethane, the organic layers combined, concentrated to ca. 3 liters (bath 50° C., 450 m bar) and the concentrated organic layer washed with 1×1 liter distilled $H_2O$ and 1×1 liter brine. The organic layer is dried with $Na_2SO_4$ and filtered through a Buchner funnel. The filtered solids are washed with 3×200 ml dichloromethane, the filtrate concentrated under vacuum (bath 50° C., 5 mm Hg) and the crude product triturated with 1 liter hexane by vigorously stirring for 1 hr. The solids are collected by filtration and washed with 2×250 ml hexane. The product is dried under high vacuum (21° C., 5 mm Hg) to yield Boc-(S)-3-[N-methyl-(2-naphthyl)-alanayl]-N-benzyl-N-methylamide: m.p.=130–131° C.

ii) A 4-necked, 3-liter, round bottomed flask, equipped with a mechanical stirrer, a nitrogen inlet-outlet and a digital thermometer is charged with 223.0 g of the product of step i) above and 400 ml dichloromethane. 400 ml trifluoroacetic acid are added to the obtained solution over 18 mins. and the whole stirred for 30 mins. at an internal temperature of 15° C., warmed to an internal temperature of 21° C. and stirred at this temperature for a further 1 hr or until all the starting material is consumed as judged by TLC. The reaction mixture is concentrated to collect any unreacted trifluoroacetic acid with appropriate cold traps (<−78° C., 20 mm Hg), and dissolved in 400 ml dichloromethane. This solution is aded over 30 mins. via a 500 ml addition funnel, while maintaining an internal temperature of 17–20° C. into a 4-necked, round bottomed flask equipped with a mechanical stirrer, thermometer and a nitrogen gas inlet, containing a pre-chilled solution of 1.5 liters of 5% NaOH (inner temperature 18° C., outer temperature 10° C.). The addition funnel is washed with 100 ml dichloromethane and the bi-phasic mixture stirred for 1 hr. The layers are separated and the aqueous layer extracted with 2×550 ml dichloromethane. (It is important to make sure both aqueous and organic layers are basic.) The combined organic layers are washed with 1×1 liter distilled $H_2O$ and 1×0.5 liters brine and concentrated (bath temperature 50°). The crude product is triturated with 700 ml hexane by vigorously stirring for 2 hrs. The solids are collected by filtration and the filtered solids washed with 3×200 ml hexane. The product is dried (21° C., 5 mm Hg) to yield the required (S)-prolyl-(S)-3-[N-methyl-(2-naphthyl)alanyl]. —N-benzyl-N-methylamide as a white solid: m.p.=120–123° C.

The formula III starting material for the above process [2-chloro-4(3H)-quinazolone] may be prepared as follows:
Process Step (e): Preparation of 2,4-dichloroguinazoline (Formula VI)

A 5-liter, 4-necked, round-bottomed flask, equipped with a mechanical stirrer, digital thermometer, addition funnel, nitrogen inlet-outlet, condenser and heating mantle is charged with 200 g benzolyleneurea (formula VII) and 1.0 liter phosphorus oxychloride. 380 g tripropylamine are added over a period of 60–65 minutes while maintaining an internal temperature below 55° C. (exothermic reaction, initial temperature: 20–22° C.). The heterogeneous mixture is refluxed (internal temperature 102–105° C.; heating mantle temperature 116–118° C.) for 3 h. The reaction mixture is cooled to 60–64° C. (internal temperature) and concentrated under reduced pressure (60–80 torr; heating mantle temperature 70–80° C.; internal temperature 60–64° C.) to collect 700–800 ml of solvent. The mixture is cooled to 40–45° C., the vaccum removed and 800 ml toluene are added. The mixture is heated to 45–50° C. (internal temperature) to obtain a brown solution. The mixture is concentrated under reduced pressure (50–60 torr; internal temperature 45–50° C.; heating mantle temperature 75–80° C.) to collect 500–600 ml of solvents. The vacuum is removed and the residue dissolved in 1.5 liters toluene. The solution is optionally allowed to stand at room temperature (20–22° C.) overnight under an atmosphere of nitrogen. A 12-liter, 4-necked, round-bottomed flask, equipped with a mechanical stirrer, digital thermometer, addition funnel, nitrogen inlet-outlet, and cooling bath is charged with 2.5 liters water, cooled to 16–18° C. (internal temperature; bath temperature 12–13° C.) and the above toluene solution is added over a period of 60–70 minutes while maintaining an internal temperature 20–24° C. (exothermic). The addition funnel is washed with a total of 300 ml toluene in two equal portions of 150 ml each and added to the mixture. The organic layer is separated and 300 ml of 5% sodium hydroxide are added over a period of 15 minutes to pH 10–11 while maintaining an internal temperature 20–23° C. (bath temperature 15–16° C.). The organic layer is separated and washed with a total of 2×1 liter water followed by 400 ml brine. The organic layer is concentrated under reduced pressure (50–100 mbar; bath temperature 48–50° C.) until no further solvent distills to give a semisolid. 2.5 liters heptane are added and the mixture cooled to room temperature (21–22° C.). The solid is collected by filtration over a Buchner funnel with suction and washed with a total of 350 ml heptane in two equal portions of 175 ml each. The solid is dried at 50–52° C. (60–65 torr) to obtain a constant weight (12 h) of the title compound as a white solid (rf=0.85/ ethylacetate).

Process Step (d): Preparation of 2-chloro-4(3H)-quinazolinone (Formula III: X=—CO—, Y=—NH—, $R^1$=Cl)

A 3-liter, 4-necked, round-bottomed flask, equipped with a mechanical stirrer, digital thermometer, addition funnel, nitrogen inlet-outlet, and cooling bath is charged with 840 ml 2N sodium hydroxide and cooled to 17–19° C. (internal temperature; bath temperature 15–17° C.). 112 g of the product of process step (e) are added in three equal portions of 37.33 g each at 10–15 minutes intervals. The resulting slurry is stirred at 21–24° C. (internal temperature; bath temperature 20–24° C.) for 4 h to obtain a solution. 560 ml water are added over a period of 5–10 minutes while maintaining an internal temperature of 21–23° C. (bath temperature 20–22° C). The whole is stirred for 5–10 minutes and 140 ml of glacial acetic acid are added over a period of 20–25 minutes while maintaining an internal temperature 20–23° C. (bath temperature 16–18° C.) with stirring. The solid is collected by filtration over a polypropylene pad filter in a Buchner funnel with suction and washed with 3×400 ml water. The solid is dried at 50–52° C. (60–65 torr) to obtain constant weight (24 h) of the title compound as a white solid (rf=0.69 in ethyl acetate).

Compounds of formula I and their pharmaceutically acceptable acid addition salts, hereinafter referred to collectively as "AGENTS OF THE INVENTION", exhibit tachykinin antagonist activity. More particularly AGENTS OF THE INVENTION exhibit potent antagonist activity at the NK-1 tachykinin (substance P) receptor. AGENTS OF THE INVENTION are accordingly useful as pharmaceuticals, e.g. as hereinafter further set forth.

TEST I: BINDING AFFINITY

Binding affinity for the NK-1 receptor may be demonstrated by ability to displace [3H]-substance P binding, e.g. as indicated in TEST I, Displacement of [$^3$H]-substance P binding from membranes from Cos-7 cells transfected with cloned human NK-1 receptor (hNK-IR) described in the aforementioned International Patent Publication no. WO 96/18643 at pages 25 through 27.

AGENTS OF THE INVENTION are active in displacing [$^3$H] Substance P in the said test method at concentrations of the order of from Ki=about 0.01 to about 10.0 nM.

Pharmacological, e.g. analgesic, utility of AGENTS OF THE INVENTION as NK-1 receptor antagonists can also be demonstrated in accordance with standard test models for example as follows:

TEST II: HYPERALGESIA MODEL

The test is performed as described for TEST II in the aforementioned International Patent Publication no. WO 96/18643 at page 28.

AGENTS OF THE INVENTION are found to be active in reducing mechanical hyperalgesia in the said test model at dosages of the order of from 0.1 to about 5.0 mg/kg p.o.

TEST III: NEUROPATHIC HYPERALGESIA MODEL

Guinea pigs are anaesthetised with enflurane in $N_2O_2O_2$ (1:1) and peripheral nerve damage is induced by partial ligation of one sciatic nerve. Following recovery from surgery, ligated animals demonstrate clear mechanical hyperalgesia measured, as in the case of TEST II employing a Vigo Basile Analgesy meter which develops within 5 days and persists for over 29 days. Groups of 6 animals receive test compound p.o. in the form of a microemulsion compsition as hereinafter described at varying dose, or placebo, 11 to 15 days following ligation. Hyperalgesia in groups receiving test compound or placebo is compared and data presented as mean ± S.E.M. and analysed using ANOVA followed by Turkey's HSD test.

AGENTS OF THE INVENTION inhibit mechanical hyperalgesia associated with peripheral nerve ligation in the above test model at doses of the order of from 0.005 to 5.0 mg/kg p.o.

AGENTS OF THE INVENTION are accordingly useful as pharmaceuticals, e.g. as tachykinin, particularly NK-1 (substance P), antagonists, e.g. for the treatment of diseases or clinical conditions characterised by or having an aetiology comprising excessive or undesirable substance-P mediated activity.

In particular they are useful as analgesics or antinociceptive agents for the treatment of pain of various genesis or aetiology. They are also useful as antiinflammatory or anti-oedemic agents for the treatment of inflammatory reactions, diseases or conditions.

In relation to their analgesic activity and in contrast with other tachykinin, e.g. NK-1, antagonists known from the art, AGENTS OF THE INVENTION have surprisingly been found to have marked or enhanced activity following oral administration. They have also and in contrast with other tachykinin, e.g. NK-1, antagonists known from the art, been found to have marked anti-nociceptive action upon the central nervous system following systemic administration, i.e. they readily penetrate the CNS.

Having regard to their analgesic/anti-inflammatory profile, AGENTS OF THE INVENTION are in particular useful for the treatment of inflammatory pain, hyperalgesia and, especially chronic pain, e.g. severe chronic pain. They are, for example useful for the treatment of pain, inflammation and/or oedema consequential to trauma, e.g. burns, sprain, fracture or the like, as well as surgical intervention, e.g. for the treatment of post-operative pain. They are further useful for the treatment of inflammatory pain of diverse genesis, e.g. for the treatment of pain associated with arthritis including rheumatoid and osteo-arthritis and rheumatic diesease, tenosynovitis, vasculitis, and rheumatic joint pain, e.g. rheumatid arthritis, as well as for the treatment of gout.

AGENTS OF THE INVENTION are further useful for the treatment of diabetic neuropathy pain and pain associated with angina, renal or billiary colic and menstruation.

AGENTS OF THE INVENTION are also useful for the treatment of migraine and of pain associated with migraine. They are further useful as anti-emetic agents, for the treatment of emesis, e.g. emesis consequential to chemotherapy, poisons, pregnancy or migraine, and irritable bowel syndrome as well as for the treatment of incontinence and gastrointestinal disorder such as retard emptying of the stomach, dyspepsia, esophageal reflux and flatulence.

AGENTS OF THE INVENTION are further indicated for use in the treatment of chronic or obstructive airways disease, e.g. for the control or prevention of bronchial oedema, pulmonary mucosal secretion or airways hyperreactivity, e.g. for use as therapeutic or prophylactic agents in the treatment of asthma. AGENTS OF THE INVENTION are indicated for use for the treatment of atopic and non-atopic asthma, e.g. for the treatment of allergic asthma, exercise induced asthma, occupational asthma, asthma following bacterial infection and drug-induced, e.g. asprin induced, asthma as well as of wheezy infant syndrome.

Further such inflammatory or obstructive airways diseases include pneumoconiosis (an inflammatory, commonly occupational, disease of the lungs, frequently accompanied by repeated inhalation of dusts) of whatever type or genesis, including, for example, aluminosis, anthracosis, asbestosis, chalicosis, ptilosis, siderosis, silicosis, tabacosis and, in particular, byssinosis.

Yet further inflammatory or obstructive airways diseases and conditions for which use of AGENTS OF THE INVENTION is indicated include adult respiratory distress syndrome (ARDS), chronic obstructive pulmonary or airways disease (COPD or COAD), and bronchitis. AGENTS OF THE INVENTION further useful for the treatment of rhinitis, e.g. for the treatment of allergic and vasomotor rhinitis.

AGENTS OF THE INVENTION are further indicated for use in the treatment of disorders of the central nervous system, in particular anxiety states, for example in the treatment of anxiety, depression, psychosis, schizophrenia, panic attack, phobias such as agrophobia, stress related somatic disorders and addiction disorders such as alcoholism or cocaine abuse;

neurodegenerative disorders such as dementia, including senile dementia, Alzheimer's disease and Down's syndrome;

demyelinating diseases such as MS, ALS and other neuropathological disorders, for example peripheral neuropathy, e.g. diabetic and chemotherapy induced neuropathy;

AGENTS OF THE INVENTION are yet further indicated for use in the treatment of diseases or conditions associated with dysfunction of the immune system, e.g. autoimmune diseases, in particular where these are associated with inflammatory, oedemic or nociceptive event. Particular diseases or conditions in this category include, for example autoimmune haematological disorders (including e.g. haemolytic anaemia, aplastic anaemia, pure red cell anaemia and idiopathic thrombocytopenia), systemic lupus erythematosus, polychondritis, scierodoma, Wegener granulamotosis, dermatomyositis, chronic active hepatitis, myasthenia gravis, psoriasis, Steven-Johnson syndrome, idiopathic sprue, autoimmune inflammatory bowel disease (including e.g. ulcerative colitis and Crohn's disease) endocrine ophthalmopathy, Graves disease, sarcoidosis, multiple sclerosis, primary billiary cirrhosis, juvenile diabetes (diabetes mellitus type I), uveitis (anterior and posterior), keratoconjunctivitis sicca and vernal keratoconjunctivitis, interstitial lung fibrosis, psoriasis, psoriatic arthritis and glomerulonephritis (with and without nephrotic syndrome, e.g. including idiopathic nephrotic syndrome or minimal change nephropathy) as well as vascuiitis. AGENTS OF THE INVENTION may also be useful as immunosuppressant or immunosuppressive adjuvents, e.g. for use in conjunction with other immunosuppressive, e.g. cyclosporin or immunosuppressive macrolide therapy, for the suppression of allograft rejection, for example following allogenic e.g. allogenic kidney, liver, corneal, heart, lung or heart-lung transplantation.

AGENTS OF THE INVENTION are yet further indicated for use in the treatment of allergic diseases or conditions, e.g. of the skin, eye, naso-pharynx or gastro intestinal tract, in particular where such disease or condition is associated with inflammatory, oedemic or nociceptive reactions. Examples of such diseases or conditions include, for example, exzema, hypersensitivity disorders such as poison ivy allergy, contact dermatitis, conjunctivitis, vernal conjunctivitis, keratoconjunctivitis sicca, urticaria and other eczemoid dermatoses.

AGENTS OF THE INVENTION are also useful in the treatment of disorders of blood flow caused by vasodilation and vasospastic diesease such as angina, migraine and Reynaud's disease.

In addition to the foregoing AGENTS OF THE INVENTION have also been found to possess P-glycoprotein blocking activity. AGENTS OF THE INVENTION are accordingly further indicated for use as adjuvent or co-therapy with drug substances of other therapeutic category for example:

for increasing or enhancing effectiveness of, or increasing or enhancing sensitivity to, other chemotherapeutic drug therapy, in particular anti-microbial (e.g. anti-bacterial, anti-viral, antifungal or anti-protozoal) chemotherapy, chemotherapy for AIDS and, especially, anti-cancer or anti-tumor (e.g. anti-neoplastic or cytostatic) chemotherapy. They are accordingly indicated for use, e.g. as a means of reducing regular chemotherapeutic dosage levels, for example, in the case of anti-neoplastic or cytostatic drug therapy, as a means of decreasing overall drug toxicity and, more especially, as a means of reversing or reducing resistance, including both inherent and acquired resistance, to chemotherapy;

to enable or potentiate other drug therapy directed at the central nervous system, e.g. to enhance drug penetration of the blood-brain barrier, for example to enable, increase or enhance other psychotropic drug therapy, e.g. for administration in conjunction with other analgesic or psychomotor stimulatory or depressant agents or agents, for example, for treatment of neurodegenerative disease including Parkinson's disease, Alzheimer's disease and so forth as well as chemotherapy to be directed at tumor of the brain;

as antiparasitic, particularly antiprotozoic, agents, e.g., particularly against organisms of the genera Toxoplasma (e.g., *Toxoplasma gondii*) and Plasmodia (e.g., *Plasmodium falciparum*).

For the above indications the dosage of AGENTS OF THE INVENTION will, of course, vary depending upon, for example, the host, the mode of administration and the nature and severity of the condition being treated as well as the relative potency of the particular AGENT OF THE INVENTION employed. However, in general, satisfactory results in animals, e.g. for the treatment of pain, migraine and emesis, are indicated to be obtained at dosages of from about 0.005 or 0.1 to about 5.0 mg/kg p.o. In larger mammals, for example humans, an indicated daily dosage is in the range of from about 0.35 or 7.0 to about 350.0 mg/day p.o., e.g. ca. 1, 10, 100 or 200 mg/day p.o. conveniently administered once or in divided doses up to 4× per day or in sustained release form. Oral dosage forms accordingly suitably comprise from about 0.1 or 3.5 to about 350 mg, e.g. about 0.25, 2.5, 25, 50, 100 or 200 mg AGENT OF THE INVENTION admixed with an appropriate pharmaceutically acceptable diluent or carrier therefor.

AGENTS OF THE INVENTION may alternatively be administered, e.g. topically in the form of a cream, gel or the like for example for the treatment of conditions of the skin as hereinbefore described or by inhalation, e.g. in dry powder form, for example for the treatment of obstructive or inflammatory airways disease, or by any other appropriate route, e.g by injection or infusion.

Pharmaceutical dosage forms as aforesaid can be manufactured employing known excipients and by methods commonly used in the art.

For oral administration AGENTS OF THE INVENTION are suitably formulated as a microemulsion preconcentrate, i.e. a formulation which, on addition to water, provides a microemulsion. Such microemulsion preconcentrates will generally comprise a hydrophilic phase (e.g. propylene glycol and/or ethanol), a hydrophobic phase (e.g. a vegetable oil mono-di-triglyceride such as commercially available under the registered trade mark MAISINE or as described in UK Patent Publication No. 2 284 615), and a surfactant (e.g. a polyoxyhydrogenated vegetable oil such as commercially available under the registered trademark CREMOPHOR e.g., CREMOPHOR RH40). The following example is illustrative of the preparation of galenic forms suitable for oral administration:

| COMPONENT | QUANTITY/UNIT DOSE |
| --- | --- |
| 1  AGENT OF THE INVENTION e.g. compound of Example 2 in free or HCl salt form | 100.0 mg |
| 2  Propylene glycol | 94.7 mg |
| 3  MAISINE | 316.9 mg |
| 4  CREMOPHOR RH 40 | 383.7 mg |
| 5  Ethanol (dehydrated) | 94.7 mg |
| Total | 993.0 mg |

The preferred AGENT OF THE INVENTION is the product of EXAMPLE 6. In one series of experiments an established $D_{30}$ for this compound in free base form and formulated as a microemulsion as hereinbefore described in TEST II above is ca. 0.45 mg/kg/p.o. at 3 hrs. respectively. A determined $D_{30}$ for aspirin in the same test method is of the order of 56.0 mg/kg/p.o. Indicated oral dosages for the said compound as an analgesic agent will thus be of the order of 1/130th. of those clinically employed using asprin.

In accordance with the foregoing the present invention also provides:

1) A pharmaceutical composition comprising an AGENT OF THE INVENTION as active ingredient together with a pharmaceutically acceptable diluent or carrier therefor; and
2) An AGENT OF THE INVENTION for use as a pharmaceutical, e.g. for use as an NK-1 (substance P) antagonist, for example for use in any particular indication hereinbefore set forth, in particular for use as an analgesic, anti-inflammatory or anti-oedemic agent or for use in treating allergic conditions or reactions, e.g. rhinitis, or in treating emesis;
3) An AGENT OF THE INVENTION for use in the manufacture of a pharmaceutical, e.g. pharmaceutical composition, e.g. for use as defined under 2) above; and
4) A method for the treatment of any disease or clinical condition characterised by or having an aetiology comprising excessive or undesirable substance-P mediated activity, for example for the treatment of any particular indication hereinbefore set forth, in a subject in need thereof which comprises administering an effective amount of e.g. a substance-P antagonist amount of, an AGENT OF THE INVENTION to said subject.

What is claimed is:

1. A compound of formula I

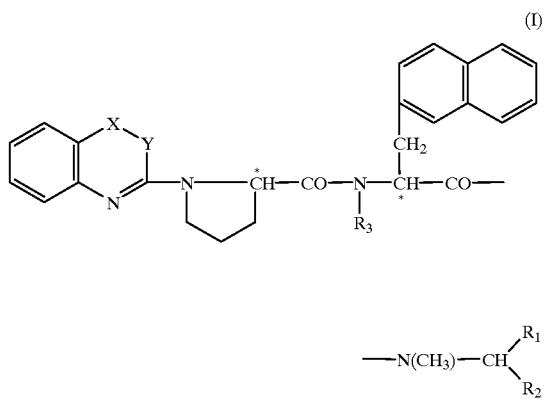

wherein
X is —CH$_2$—, —CO— or a direct linkage,
Y is —O—, —S— or —NH—,
R$_1$ is phenyl,
R$_2$ is hydrogen or phenyl, and
R$_3$ is hydrogen or methyl,
or acid addition salt thereof.

2. A compound according to claim 1 wherein, X is —CO—, Y is —NH—, R$_2$ is hydrogen and R$_3$ is methyl, or acid addition salt thereof.

3. A compound according to claim 1 wherein,
R$_2$ and R$_3$ are each hydrogen and
a) X is —CO— and Y is —O—, or
b) X is —CO—, Y is —NH—,
c) X is a direct linkage and Y is —O— or —NH— or
d) X is —CH$_2$— and Y is —O—,
or acid addition salt thereof.

4. A compound according to claim 1 wherein, in formula I, the carbon atoms marked with an asterisk (*) both have the S-configuration, or acid addition salt thereof.

5. The compound according to claim 4 wherein, X is —CO—, Y is —NH—, R$_2$ is hydrogen, R$_3$ is methyl, or acid addition salt thereof.

6. Process for the production of a compound of formula I as defined in claim 1, or acid addition salt thereof, which process comprises:
a) reacting a compound of formula II

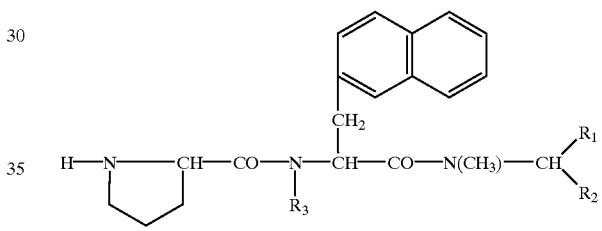

wherein R$_1$ to R$_3$ have the meanings given in claim 1, with a compound of formula III

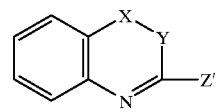

wherein Y has the meanings given in claim 1 and Z' is a leaving group;
b) for the production of a compound of formula I, wherein X is —CO— and Y is —O— or —S—, reacting a compound of formula II as defined above with a compound of formula IV

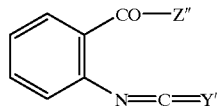

wherein Z" is a leaving group and Y$^1$ is —O— or —S—; or
c) for the production of a compound of formula I, wherein X is —CO— and Y is —NH—, treating a compound of formula V

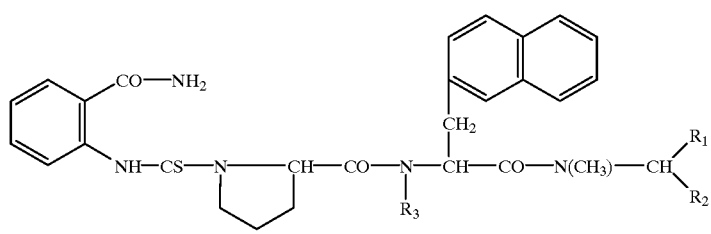

(V)

wherein $R_1$, $R_3$ have the meanings given in claim 1, with an alkyl halide; and recovering the compound of formula I thus obtained in free or acid addition salt form.

7. A process according to claim 6 for the production of a compound of formula I wherein X is —CO—, Y is —NH—, $R_2$ is hydrogen and $R_3$ is methyl, or acid addition salt thereof, comprising reaction of the corresponding compound of formula II as illustrated in claim 6 with a compound of formula III as illustrated in claim 6 wherein X and Y have the meanings given above and $Z^1$ is halogen.

8. A pharmaceutical composition comprising a compound as claimed in according to claim 1 or pharmaceutically acceptable acid addition salt thereof, together with a pharmaceutically acceptable diluent or carrier therefor.

9. A method for the treatment of pain in a subject in need thereof which method comprises administering to said subject an analgesically effective amount of a compound according to claim 1 or a pharmaceutically acceptable acid addition salt thereof.

* * * * *

UNITED STATES PATENT AND TRADEMARK OFFICE
CERTIFICATE OF CORRECTION

PATENT NO : 6,107,293
DATED: : August 22, 2000
INVENTOR(S) : WALPOLE ET AL.

It is certified that there is an error in the above-identified patent and that said Letters Patent is hereby corrected as shown below:

In claim 8, line 2, "as claimed in" should be deleted.

Signed and Sealed this

Seventeenth Day of April, 2001

*Attest:*

NICHOLAS P. GODICI

*Attesting Officer*  *Acting Director of the United States Patent and Trademark Office*